United States Patent [19]

Emonds-Alt et al.

[11] Patent Number: 5,656,639

[45] Date of Patent: Aug. 12, 1997

[54] HETEROCYCLIC COMPOUNDS, METHOD OF PREPARING THEM AND PHARMACEUTICAL COMPOSITIONS IN WHICH THEY ARE PRESENT

[75] Inventors: Xavier Emonds-Alt, Combaillaux; Isabelle Grossriether, Paris; Vincenzo Proietto, Saint Georges d'Orques; Didier Van Broeck, Murviel les Montpellier, all of France

[73] Assignee: Sanofi, Paris, France

[21] Appl. No.: 593,929

[22] Filed: Jan. 30, 1996

[30] Foreign Application Priority Data

Jan. 30, 1995 [FR] France .................... 95 01015

[51] Int. Cl.$^6$ .................... A61K 31/44; A61K 31/55; C07D 453/02
[52] U.S. Cl. .................... 514/305; 514/212; 540/531; 546/133
[58] Field of Search .................... 546/133; 514/305, 514/212; 540/531

[56] References Cited

U.S. PATENT DOCUMENTS 5,340,822  8/1994  Emonds-Alt .................... 514/316

FOREIGN PATENT DOCUMENTS 0 512 901  11/1991  European Pat. Off. .
0 591 040  4/1994  European Pat. Off. .

*Primary Examiner*—C. Warren Ivy
*Assistant Examiner*—Evelyn Huang

*Attorney, Agent, or Firm*—Bacon & Thomas

[57] ABSTRACT

The invention relates to compounds of the formula

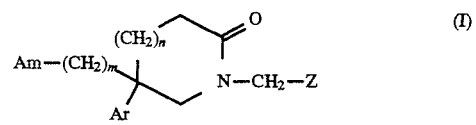

in which:
m is 2 or 3;
n is 0, 1 or 2;
Am is

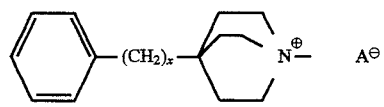

$R_1$ is a ($C_1$–$C_4$)-alkyl or a benzyl;
$R_2$ is a substituted or unsubstituted phenyl;
x is zero or one;
Ar is a substituted or unsubstituted phenyl, a naphthyl or an indolyl;
Z is a substituted or unsubstituted phenyl; and
$A^\ominus$ is an anion;
the salts thereof, where appropriate, with mineral or organic acids and the solvates thereof, where appropriate.

These compounds have a strong affinity for the $NK_1$ receptor and are useful for preparing drugs for the treatment of substance P-dependent pathological conditions.

19 Claims, No Drawings

HETEROCYCLIC COMPOUNDS, METHOD OF PREPARING THEM AND PHARMACEUTICAL COMPOSITIONS IN WHICH THEY ARE PRESENT

The present invention relates to novel heterocyclic compounds, to a method of preparing them and to the pharmaceutical compositions in which they are present as the active principle.

More particularly, the present invention relates to a novel class of aromatic compounds for therapeutic use in pathological phenomena involving the tachykinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, I. S. and Pernow ed., 287–293, Raven Press, New York), gastrointestinal disorders (D. Regoli et al., Trends Pharmacol. Sci., 1985, 6, 481–484), respiratory disorders (J. Mizrahi et al., Pharmacology, 1982, 25, 39–50), neurological disorders and neuropsychiatric disorders, these examples being neither limiting nor exclusive.

In recent years, numerous research studies have been carried out on tachykinins and their receptors. Tachykinins are distributed throughout both the central nervous system and the peripheral nervous system. The tachykinin receptors have been recognized and are classified into three types: $NK_1$, $NK_2$, $NK_3$. Substance P (SP) is the endogenous ligand of the $NK_2$ receptors, neurokinin A ($NK_A$) that of the $NK_2$ receptors and neurokinin B ($NK_B$) that of the $NK_3$ receptors.

The $NK_1$, $NK_2$ and $NK_3$ receptors have been identified in different species. A review by C. A. Maggi et al. looks at the tachykinin receptors and their antagonists and gives an account of the pharmacological studies and the applications in human therapeutics (J. Autonomic Pharmacol., 1993, 13, 23–93).

The following non-peptide compounds may be mentioned among the antagonists specific for the $NK_1$ receptor: CP-96345 (J. Med. Chem., 1992, 35, 2591–2600), RP-68651 (Proc. Natl. Acad. Sci. USA, 1991, 88, 10208–10212), SR 140333 (Curr. J. Pharmacol., 1993, 250, 403–413).

Numerous patents or patent applications describe compounds which are active on the tachykinin receptors. Thus European patent application 0 512 901 relates to compounds of the formula $$Y-(CH_2)_{m'}-C \overset{(CH_2)_{n'}}{\underset{(CH_2)_{p'}}{\diagdown}} \overset{Q'}{\underset{Ar'}{\diagup}} N-T'-(CH_2)_q-Z' \qquad 1$$

in which particularly:

Q' is an oxygen atom or two hydrogen atoms;

T'=—C(O)— or —CH$_2$—; and

Y can be a group $$Ar'-(CH_2)_{x'}-\overset{}{\underset{X'}{\diagdown}} N-$$

in which:

Ar' is an optionally substituted phenyl;
x'=0 or 1; and

X' is hydrogen, a hydroxyl group or another monovalent radical;

and the quaternary ammonium salts with the piperidine nitrogen.

Said patent application does not describe any compounds of formula 1 in which simultaneously Q' is oxygen and Y is a 4-phenylpiperidine or 4-benzylpiperidine group which is in the form of a quaternary ammonium salt with the piperidine nitrogen, or any compounds of formula 1 in which simultaneously Q' is oxygen, n'=p'=1, Y is a 4-phenylpiperidine, 4-benzylpiperidine, 4-hydroxy-4-phenylpiperidine or 4-hydroxy-4-benzylpiperidine group and —T'—(CH$_2$)$_q$—Z' is a substituted benzyl.

European patent application 0 591 040 relates to compounds of the formula $$Ar_1-T_1-CO-N-CH_2-\overset{R'_1}{\underset{Ar'_1}{\overset{|}{C}}}-CH_2-CH_2-Am_1^{\oplus}, A_1^{\ominus} \qquad 2$$

in which particularly:

Ar$_1$ is an optionally substituted mono-, di- or tri-cyclic aromatic or heteroaromatic group;

T$_1$ is a direct bond or a hydroxymethylene, alkoxymethylene or alkylene group;

Ar'$_1$ is a substituted or unsubstituted phenyl; a thienyl; a benzothienyl; a naphthyl; or an indolyl;

Am$^{\oplus}_1$ is the radical $$X_2-\overset{X_1}{\underset{X_3}{\overset{|}{N^{\oplus}}}}-$$

in which $X_1$, $X_2$ and $X_3$, together with the nitrogen atom to which they are bonded, form an azabicyclic or azatricyclic system, for example the 4-phenyl-1-azoniabicyclo[2.2.2] octane group;

R'$_1$ has different meanings or is hydrogen; and

Q'$_1$ is hydrogen, or

Q'$_1$ and R'$_1$ together form a 1,2-ethylene, 1,3-propylene or 1,4-butylene group.

Non-peptide compounds have now been found which have a very strong affinity for the $NK_1$ receptor and a high specificity for said receptor. These compounds can be used to prepare drugs which are useful in the treatment of any substance P-dependent pathological condition.

Very strong affinity for the human $NK_1$ receptor is understood as meaning an affinity characterized by an inhibition constant Ki of less than $5.10^{-9}$ M.

In ligand binding studies, the inhibition constant Ki is defined by the Cheng-Prusoff relationship (in Receptor Binding in Drug Research, eds. R. A. O'Brien, Marcel Dekker, New York, 1986):

$$Ki = \frac{IC_{50}}{1+\frac{[L]}{Kd}}$$

[L]: concentration of the ligand,

Kd: dissociation constant of the ligand,

IC$_{50}$: concentration which inhibits the ligand binding by 50%.

High specificity for the human $NK_1$ receptor is understood as meaning that the inhibition constant (Ki) for the human $NK_1$ receptor is at least 100 times lower than the inhibition constant (Ki) for the $NK_2$ receptor or for the $NK_3$ receptor.

Thus, according to one of its features, the present invention relates to compounds of the formula

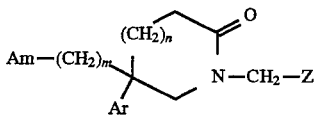

in which:

m is two or three;

n is 0, 1 or 2;

Am is a group selected from:

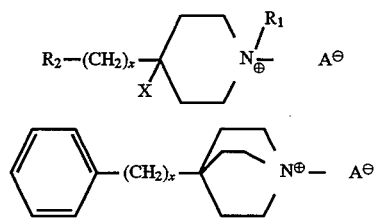

and if n=0, Am can also be the group c)

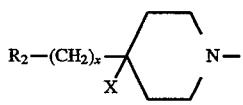

$R_1$ is a $(C_2-C_4)$-alkyl or a benzyl;

$R_2$ is a phenyl which is unsubstituted or monosubstituted or polysubstituted by a halogen atom, a hydroxyl, a $(C_1-C_4)$-alkoxy, a $(C_1-C_4)$-alkyl or a trifluoromethyl, said substituents being identical or different;

X is a hydrogen atom or a hydroxyl group;

x is zero or one;

Ar is a phenyl which is unsubstituted or monosubstituted or polysubstituted by a halogen atom; a naphthyl; or an indolyl;

Z is a phenyl which is monosubstituted or polysubstituted by a halogen atom, a $(C_1-C_4)$-alkyl or a trifluoromethyl; and $A^\ominus$ is an anion;

the salts thereof, where appropriate, with mineral or organic acids and the solvates thereof, where appropriate.

The compounds of formula (I) according to the invention include both the optically pure isomers and the racemates, as well as the axial and equatorial isomers if Am has the value a).

If Am is c), it is possible to form salts of the compounds of formula (I). These salts include those with mineral or organic acids which permit a suitable separation or crystallization of the compounds of formula (I), such as picric or oxalic acid or an optically active acid, for example a mandelic or camphosulfonic acid, and mineral or organic acids which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, benzenesulfonate, gluconate, citrate, isethionate or p-toluenesulfonate.

The anions are those normally used to salify quaternary ammonium ions and are preferably chloride, bromide, iodide, acetate, hydrogensulfate, methanesulfonate, paratoluenesulfonate and benzenesulfonate ions.

It is preferable to use the pharmaceutically acceptable anions, for example the chloride, methanesulfonate, paratoluenesulfonate or benzenesulfonate.

In the present description, the alkyl groups or alkoxy groups are linear or branched; halogen atom is understood as meaning a chlorine, bromine, fluorine or iodine atom.

Advantageously, the present invention relates to the compounds of formula (I) in which m=2.

The compounds of formula (I) in which Z is a group selected from dimethylphenyl, trifluoromethylphenyl and bistrifluoromethylphenyl are preferred compounds according to the invention.

According to the present invention, the preferred compounds are those of formula (I) in which:

Ar is a 3,4-dichlorophenyl or a 3,4-difluorophenyl;

Z is a 3,5-dimethylphenyl, a 3,5-bis(trifluoromethyl) phenyl or a 2,4-bis(trifluoromethyl)phenyl;

either n=0, 1 or 2 and Am is a) or b), or n=0 and Am is c); and $A^\ominus$ is a pharmaceutically acceptable anion.

According to the present invention, the compounds of the formula

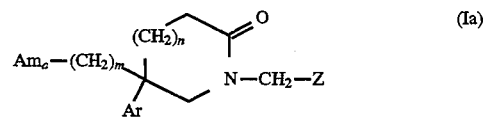

in which $Am_a$ is the group b) as defined for (I) and n, m, Ar and Z are as defined for (I), and the solvates thereof, where appropriate, are also preferred.

The pharmaceutically acceptable salts of the compounds of the formula

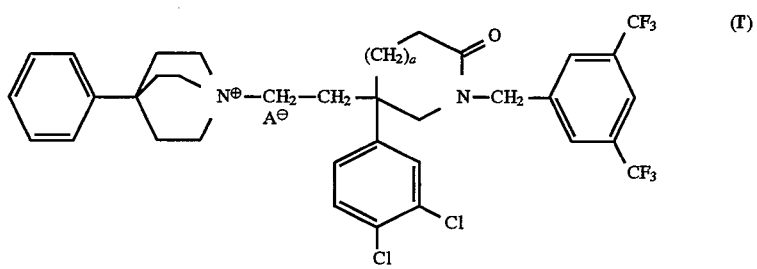

in which a is 0 or 1, and the solvates thereof, where appropriate, are very particularly preferred.

According to another of its features, the present invention relates to a method of preparing the compounds of formula (I), which comprises:

1) treating a compound of the formula

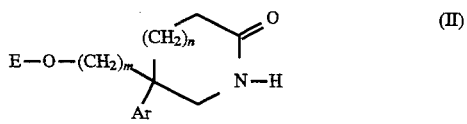

in which m, n and Ar are as defined for (I) and E is an O-protecting group such as tetrahydropyran-2-yl, benzoyl or a $C_1$-$C_4$-acyl,
with a halogenated derivative of the formula

in which Z is as defined for (I) and Hal is a halogen atom, preferably bromine or chlorine;

2) converting the O-protecting group to a hydroxyl group by reaction with an acid or a base;

3) treating the resulting alcohol of the formula

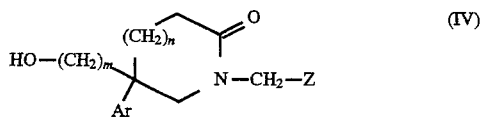

in which Ar, Z, m and n are as defined above, with methanesulfonyl chloride, benzenesulfonyl chloride, paratoluenesulfonyl chloride or trifluoromethanesulfonyl chloride;

4) reacting the resulting compound of the formula

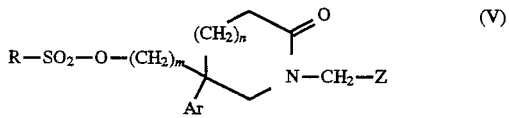

in which R is a methyl, phenyl, paratolyl or trifluoromethyl group,
with a secondary or tertiary amine AmH or Am, in an organic solvent, at a temperature between room temperature and 120° C.; and 5) isolating the resulting product, optionally exchanging the sulfonate anion with another anion and optionally converting the resulting product to a salt thereof.

In step 2, the deprotection is effected in an acid medium, for example in the presence of hydrochloric acid if E is a tetrahydropyran-2-yl, or in a basic medium, for example in the presence of sodium hydroxide or lithium hydroxide if E is a benzoyl or a $C_1$-$C_4$-acyl.

In the last step, the sulfonate anion can be exchanged, in situ or after isolation of the compound of formula (I) in which $A^{\ominus}$ is the sulfonate ion, with another anion $A^{\ominus}$ by the conventional methods, for example by exchange in solution with saturated sodium chloride solution or with hydrochloric acid solution if $A^{\ominus}$ is a chloride anion, or by exchange of the anion via elution of the compound (I) on an ion exchange resin, for example Amberlite IRA68 or Duolite A375.

If Am is a group a), the quaternary ammonium salts formed with the piperidine nitrogen are prepared by reacting the free bases of the compounds of formula (I) with an excess of an alkylating agent of the formula A-$R_1$, in which A is as defined above for (I), preferably a chloride or an iodide, and $R_1$ is as defined above for (I), and the reaction mixture is heated in a solvent, for example dichloromethane, chloroform, acetone or acetonitrile, at a temperature between room temperature and the reflux temperature, for one to several hours, to give a mixture of the axial and equatorial isomers of the quaternary ammonium salts after treatment by the customary methods. Preferably, $A^{\ominus}$ is an iodide, which can be exchanged with another anion or with a pharmaceutically acceptable anion, for example via elution of the compound (I) on an ion exchange resin such as Amberlite IRA68 or Duolite A375. The isomers are separated by the customary methods, for example by chromatography or recrystallization.

Resolution of the racemic mixtures of compounds (I) or of intermediates such as (IV) makes it possible to isolate the enantiomers by using methods known to those skilled in the art.

The compounds of formula (II) are prepared by the methods described in EP-A-0 512 901.

The halogenated derivatives of formula (III) are known or are prepared by known methods.

4-Phenylpiperidine, 4-benzylpiperidine, 4-hydroxy-4-phenylpiperidine and 4-hydroxy-4-benzylpiperidine are commercially available.

4-Phenyl-1-azabicyclo[2.2.2]octane, or 4-phenylquinuclidine, and 4-benzyl-1-azabicyclo[2.2.2]-octane, or 4-benzylquinuclidine, are prepared according to T. Perrine, J. Org. Chem., 1957, 22, 1484–1489.

The compounds of formula (I) above also include those in which one or more hydrogen, carbon, fluorine or iodine atoms have been replaced with their radioactive isotope, for example tritium, carbon-14, fluorine-19 or iodine-125. Such labeled compounds are useful in research, metabolic or pharmacokinetic studies or in biochemical tests as receptor ligands, and can be used as pharmacological tools in man or animals.

The compounds according to the invention were subjected to biochemical tests.

The affinity of the compounds of formula (I) for the tachykinin receptors was evaluated in vitro by several biochemical tests using radioligands:

1°) The binding of [$^{125}$I]BH-SP (substance P labeled with iodine-125 using Bolton-Hunter's reagent) to the $NK_1$ receptors of human lymphoblasts.

2°) The binding of [$^{125}$I]His-$NK_A$ to the $NK_2$ receptors of the rat duodenum or bladder.

3°) The binding of [$^{125}$I]His[MePhe$^7$]$NK_B$ to the $NK_3$ receptors of the rat cerebral cortex, the guineapig cerebral cortex and the gerbil cerebral cortex, and to the human $NK_3$ cloned receptors expressed by CHO cells (Buell et al., FEBS Letters, 1992, 299, 90–95).

The tests were performed according to X. Emonds-Alt et al. (Eur. J. Pharmacol., 1993, 250, 403–413).

The compounds according to the invention strongly inhibit binding to the $NK_1$ receptors of IM9 human lymphoblasts. The inhibition constant Ki for the lymphoblast receptors is less than $5.10^{-9}$M. For the same compounds, it was found that the inhibition constant (Ki) for the human $NK_3$ cloned receptors is greater than or equal to $10^{-7}$M and that the inhibition constant (Ki) for the $NK_2$ receptor of the rat duodenum or bladder is greater than or equal to $10^{-7}$M.

The activity of the compounds according to the present invention as inhibitors of binding to the $NK_1$ receptors is distinctly greater than that of similar compounds described in the prior art.

Thus the inhibition constant Ki of the axial isomer of 1-methyl-1-[2-[1-[3,5-bis(trifluoromethyl)-benzyl[- 5-(3,4-dichlorophenyl)-2-oxopiperid-5-yl]-ethyl]-4-phenylpiperidinium iodide for the binding of substance P to the human lymphoblast receptor is of the order of $0.1.10^{-9}$M, whereas the inhibition constant Ki of 5-[2-(4-benzyl-1-piperid-1-yl)ethyl]-5-(3,4-dichlorophenyl)-1- benzylpiperid-2-one hydrochloride, described in Example 1 of patent application EP-0 512 901 (compound unsubstituted on the benzyl), is of the order of $10^{-6}$M, measured under the same conditions.

Likewise, the inhibition constant Ki of 4-(3,4-dichlorophenyl)-4-[2-(4-hydroxy-4-phenylpiperid-1-yl)-ethyl]-1-]3,5-bis(trifluoromethyl)benzyl]pyrrolidin-2-one hydrochloride for the binding of substance P to the human lymphoblast receptor is of the order of $0.1.10^{-9}$M, whereas the Ki of 1-benzyl-4-(3,4-dichlorophenyl)-4-[2-(4-hydroxy-4-phenylpiperid-1-yl)ethyl]piperid-2-one hydrochloride, described in Example 3 of patent application EP-0 512 901, is of the order of $10^{-6}$M, measured under the same conditions.

In particular, the compounds of the present invention are active principles of pharmaceutical compositions, the toxicity of which is compatible with their use as drugs.

The compounds of formula (I) above can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.5 to 1000 mg per day, depending on the age of the subject to be treated or the type of treatment: prophylactic or curative.

For their use as drugs, the compounds of formula (I) are generally administered in dosage units. Said dosage units are preferably formulated as pharmaceutical compositions in which the active principle is mixed with a pharmaceutical excipient.

Thus, according to another of its features, the present invention relates to pharmaceutical compositions in which a compound of formula (I) is present as the active principle.

In the pharmaceutical compositions of the present invention for oral, sublingual, inhalational, subcutaneous, intramuscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

When a solid composition in the form of tablets is prepared, the main active principle is mixed with a pharmaceutical vehicle such as silica, gelatin, starch, lactose, magnesium stearate, talc, gum arabic or the like. The tablets can be coated with sucrose, various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester, and incorporating the mixture obtained into soft or hard gelatin capsules.

A preparation in the form of a syrup or elixir can contain the active principle together with a sweetener, which is preferably calorie-free, methylparaben and propylparaben as an antiseptic, a flavoring and an appropriate color.

The water-dispersible granules or powders can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol or butylene glycol.

Administration by inhalation is effected using an aerosol which contains for example sorbitan trioleate or oleic acid, as well as trichlorofluoromethane, dichlorofluoromethane, dichlorotetrafluoroethane or any other biologically compatible propellant gas; it is also possible to use a system containing the active principle in powder form, by itself or associated with an excipient.

The active principle can also be formulated as microcapsules, with one or more carriers or additives if appropriate.

In each dosage unit, the active principle of formula (I) is present in the amounts appropriate to the daily doses envisaged. In general, each dosage unit is suitably adjusted according to the dosage and the intended type of administration, for example tablets, gelatin capsules and the like, sachets, ampoules, syrups and the like, and drops, so that such a dosage unit contains from 0.5 to 1000 mg of active principle, preferably from 2.5 to 250 mg, to be administered one to four times a day.

According to another of its features, the present invention relates to the use of the products of formula (I) for the preparation of drugs intended for the treatment of physiological disorders associated with an excess of tachykinins, especially substance P, and all substance P-dependent pathological conditions of the respiratory, gastrointestinal, urinary, immune, cardiovascular and central nervous systems, as well as pain and migraine.

Non-limiting examples are:

acute and chronic pain associated for example with migraine, with pains experienced by cancer and angina patients, and with chronic inflammatory processes such as osteoarthritis and rheumatoid arthritis, inflammations such as obstructive chronic respiratory diseases, asthma, allergies, rhinitis, coughs, bronchitis, hypersensitivity, for example to pollen and mites, rheumatoid arthritis, osteoarthritis, psoriasis, ulcerative colitis, Crohn's disease, inflammation of the intestines (irritable colon), prostatitis, nervous bladder, cystitis, urethritis and nephritis, diseases of the immune system associated with suppression or stimulation of the functions of the immune cells, for example rheumatoid arthritis, psoriasis, Crohn's disease, diabetes and lupus, diseases of the central nervous system of the neuropsychiatric or neurological type, such as anxiety, depression, psychosis, schizophrenia, mania, dementia, epilepsy, Parkinson's disease, Alzheimer's disease, drug dependence, Down's syndrome and Huntington's chorea, as well as neurodegenerative diseases, diseases of the gastrointestinal system, such as nausea, vomiting, irritable colon, gastric and duodenal ulcers, diarrhea and hypersecretions, diseases of the cardiovascular system, such as hypertension, the vascular aspects of migraine, edema, thrombosis, angina pectoris and vascular spasms, and heart rate and rhythm disorders, in particular those caused by pain or stress.

The present invention also includes a method of treating said complaints at the doses indicated above.

The following abbreviations are used in the Preparations and in the Examples:

EtOH: ethanol
MeOH: methanol
Ether: diethyl ether
Iso ether: diisopropyl ether
DMF: dimethylformamide
AcOEt: ethyl acetate
DCM: dichloromethane
THF: tetrahydrofuran
NaOH: sodium hydroxide
$KHCO_3$: potassium hydrogencarbonate
$NaHCO_3$: sodium hydrogencarbonate
NaCl: sodium chloride
Triton B: 40% solution of N-benzyltrimethylammonium hydroxide in MeOH
$Na_2SO_4$: sodium sulfate
$MgSO_4$: magnesium sulfate
iPr: isopropyl
RT: room temperature
M.p.: melting point
NMR: nuclear magnetic resonance
s: singlet
ds: double singlet
d: doublet
sept: septuplet
u: unresolved signals
mult: multiplet

PREPARATION 1

5-(3,4-Dichlorophenyl)-5-[2-(tetrahydropyran-2-yloxy) ethyl]piperid-2-one

A) 2-(3,4-Dichlorophenyl)-4-(tetrahydropyran-2-yloxy) butanenitrile 20 g of sodium hydride as a 55–60% dispersion in oil are suspended in 200 ml of dry tetrahydrofuran. A solution of 85 g of 3,4-dichlorophenylacetonitrile in 500 ml of THF is added dropwise at 20° C. in 30 minutes and the reaction mixture is then stirred at RT for 2 hours. It is cooled to −20° C., a solution of 98 g of 2-(2-bromoethoxy)tetrahydropyran in 100 ml of THF is added, the mixture is allowed to return to RT and, after 2 hours, a solution of 50 g of ammonium chloride in 3 liters of water is added. Extraction is carried out with 1.5 liters of ether and the extract is washed with saturated sodium chloride solution, decanted, dried over $MgSO_4$ and concentrated under vacuum.

The residue is chromatographed on silica gel using dichloromethane as the eluent. The pure product fractions are concentrated under vacuum to give 83.6 g of an oil.

B) Ethyl 4-cyano-4-(3,4-dichlorophenyl)-6-(tetrahydropyran-2-yloxy)hexanoate 21 g of the nitrile prepared above according to A) are dissolved in 100 ml of THF, a solution of 0.067 mol of lithium diisopropylamide in 100 ml of THF is then added dropwise at room temperature and the reaction mixture is stirred for one hour at RT. 12 g of ethyl 3-bromopropionate are then added and the mixture is heated at 50° C. for two hours. It is cooled, poured into saturated ammonium chloride solution and extracted with ether, the extract is then washed with water and the ether phase is separated off by decantation, dried over $Na_2SO_4$ and concentrated under vacuum. The residue is purified by chromatography on silica gel using dichloromethane/ethyl acetate (100/1; v/v) as the eluent. Concentration of the pure fractions gives 13 g of the expected compound.

C) 5-(3,4-Dichlorophenyl)-5-[2-(tetrahydropyran-2-yloxy)ethyl]piperid-2-one 13 g of the compound prepared above are dissolved in 250 ml of ethanol and 40 ml of aqueous ammonia and are hydrogenated at room temperature and atmospheric pressure in the presence of Raney® nickel. When the theoretical volume of hydrogen has been absorbed, the mixture is filtered on Célite® and the filtrate is concentrated under vacuum. The residue is taken up with water and extracted with ether and the ether phase is then washed with water, dried over $MgSO_4$ and concentrated under vacuum to give 9 g of the expected product.

PREPARATION 2

5-[2-(Tetrahydropyran-2-yloxy)ethyl]-5-(3,4-difluorophenyl)piperid-2-one

A) 2-(3,4-Difluorophenyl)-4-(tetrahydropyran-2-yloxy) butanenitrile 14.4 g of sodium hydride as a 60% dispersion in oil are suspended in 250 ml of THF and cooled in a water bath. A solution of 50 g of 3,4-difluorophenylacetonitrile in 50 ml of THF is added dropwise, the mixture is then left to stand for 3 hours at RT and a solution of 68.16 g of 2-(2-bromoethoxy)tetrahydropyran in 100 ml of THF is added dropwise. After one night at RT, the mixture is acidified with a buffer of pH 2, the THF is evaporated off and the residue is taken up with water and extracted with ether. The extract is washed twice with a buffer solution of pH 4 and then with water and with saturated sodium chloride solution. It is decanted and the organic phase is dried over $MgSO_4$ and concentrated under vacuum. The residue is chromatographed on silica using pure toluene and then toluene containing up to 3% of AcOEt as the eluent to give 49.5 g of the expected product.

B) Methyl 6-(tetrahydropyran-2-yloxy)-4-(3,4-difluorophenyl)-4-cyanohexanoate

The product obtained in the previous step (28.12 g) is placed in 100 ml of THF, 1 ml of Triton B is added, the mixture is heated to the reflux temperature and 9.46 g of methyl acrylate are then added dropwise. The mixture is allowed to return to RT, the solvent is evaporated off and the residue is taken up with water and extracted with ether. The extract is washed twice with water, twice with a buffer solution of pH 4, with water and then with saturated sodium chloride solution. It is decanted and the organic phase is dried over $MgSO_4$ and concentrated under vacuum to give 34.6 g of the expected product.

C) 5-[2-(Tetrahydropyran-2-yloxy)ethyl]-5-(3,4-difluorophenyl)piperid-2-one

The product obtained in the previous step (34.6 g) is dissolved in 500 ml of 95° EtOH. 5 g of solid $KHCO_3$ and then Raney® nickel are added. The mixture is hydrogenated at 60° C. under 20.4 bar. After 4 hours, it is filtered on Célite® and the solvent is evaporated off. The residue is taken up with water and extracted with AcOEt and the extract is washed twice with water and with saturated sodium chloride solution. The organic phase is dried over $MgSO_4$ and concentrated under vacuum to give 32 g of the expected product.

PREPARATION 3

6-(3,4-Dichlorophenyl)-6-[2-(tetrahydropyran-2-yloxy) ethyl]perhydroazepin-2-one A) Ethyl 5-cyano-5-(3,4-dichlorophenyl)pentanoate 5.9 g of sodium hydride as a 55% dispersion in oil are suspended in 50 ml of THF; the suspension is cooled in an ice bath and 25 g of 3,4-dichlorophenylacetonitrile in 25 ml of THF are added dropwise; the mixture is cooled again in an ice bath and a solution of 26.21 g of ethyl 4-bromobutanoate in 25 ml of THF is added dropwise. After one night at RT, the mixture is evaporated to dryness and the residue is then taken up with 2N hydrochloric acid solution and extracted with ether. The extract is washed with 2N hydrochloric acid solution and then with saturated sodium chloride solution. The organic phase is dried over $MgSO_4$ and then concentrated under vacuum and the residue is chromatographed on silica using pure toluene up to a toluene/AcOEt mixture (100/3; v/v) as the eluent to give 17 g of the expected product.

B) Ethyl 5-cyano-5-(3,4-dichlorophenyl)-7-(tetrahydropyran-2-yloxy)heptanoate 2.5 g of sodium hydride as a 55% dispersion in oil are suspended in 50 ml of DMF and cooled to −20° C. and a mixture of 11.8 g of 2-(2-bromoethoxy)tetrahydropyran and 17 g of the compound obtained in the previous step in 50 ml of DMF is added dropwise. After one night at RT, the mixture is evaporated to dryness and the residue is taken up with a buffer solution of pH 4 and then extracted with AcOEt. The extract is washed with a buffer solution of pH 4, with water and then with saturated sodium chloride solution. The organic phase is dried over $MgSO_4$ and then concentrated and the residue is chromatographed on silica using pure toluene up to a toluene/AcOEt mixture (100/10; v/v) as the eluent to give 15.4 g of the expected product.

C) Ethyl 5-(aminomethyl)-5-(3,4-dichlorophenyl)-7-(tetrahydropyran-2-yloxy)heptanoate The product obtained in the previous step (15.4 g) is dissolved in 200 ml of MeOH, 25 ml of a saturated solution of ammonia in MeOH are added and the mixture is then hydrogenated at 40° C. under atmospheric pressure in the presence of Raney® nickel. The catalyst is filtered off, the filtrate is evaporated to dryness and the residue is taken up with ether. The mixture is washed with water and with saturated sodium chloride solution, dried over $MgSO_4$ and concentrated under vacuum to give 12.8 g of the expected product.

D) 6-(3,4-Dichlorophenyl)-6-[2-(tetrahydropyran-2-yloxy)ethyl]perhydroazepin-2-one The product obtained in the previous step (12.8 g) is dissolved in 200 ml of xylene and refluxed for 48 hours. It is evaporated to dryness and the residue is then chromatographed on silica using pure DCM up to a DCM/MeOH mixture (98/2; v/v) as the eluent to give 10.1 g of the expected product.

PREPARATION 4

4-(3,4-Dichlorophenyl)-4-[2-(tetrahydropyran-2-yloxy)ethyl]pyrrolidin-2-one

A) 2-(3,4-Dichlorophenyl)-4-(tetrahydropyran-2-yloxy)butanenitrile

This compound is prepared in Preparation 1, step A.

B) Ethyl 3-cyano-3-(3,4-dichlorophenyl)-5-(tetrahydropyran-2-yloxy)pentanoate 57 g of the compound of step A are dissolved in 150 ml of DMF. 7.85 g of sodium hydride as a 55% dispersion in oil are added in small portions. After heating for 1 hour at 60° C., the mixture is cooled to RT and 30.8 g of ethyl bromoacetate in 50 ml of DMF are added dropwise. After stirring for 2 hours at RT, the DMF is evaporated off under reduced pressure, the residue is extracted with ether and the extract is then washed with water until the pH of the washings is neutral. After drying over $MgSO_4$ and evaporation of the solvents, the residue is chromatographed on silica using a DCM/AcOEt mixture (95/5; v/v) as the eluent to give 29 g of the expected compound.

C) 4-(3,4-Dichlorophenyl)-4-[2-(tetrahydropyran-2-yloxy)ethyl]pyrrolidin-2-one

A solution of 8 g of the compound obtained in step B in 100 ml of 100° EtOH, 5 ml of water and 0.6 g of $NaHCO_3$ is hydrogenated at atmospheric pressure and at RT. The catalyst is filtered off and the filtrate is evaporated under vacuum. The residue is extracted with DCM, the extract is washed with water and dried over $MgSO_4$ and the solvent is evaporated off under vacuum to give 6 g of the expected product.

PREPARATION 4 BIS 4-(3,4-Dichlorophenyl)-4-[2-(tetrahydropyran-2-yloxy)ethyl]pyrrolidin-2-one A) Diethyl 3-cyano-3-(3,4-dichlorophenyl)pentane-1,5-dioate 4.3 g of sodium hydride as a 60% dispersion in oil are added to a solution of 10 g of 3,4-dichlorophenylacetonitrile in 50 ml of THF and the mixture is stirred until the evolution of hydrogen has ceased. It is cooled to 0° C. and a solution of 18 g of ethyl bromoacetate in 50 ml of THF is added dropwise. The mixture is allowed to return to RT and stirred overnight. It is evaporated to dryness, the residue is taken up with ether and the mixture is washed with a buffer solution of pH 2 and dried over MgSO. The residue is chromatographed on silica using a DCM/AcOEt mixture (80/20; v/v) as the eluent to give 15 g of the expected compound.

B) 4-(3,4-Dichlorophenyl)-4-(ethoxycarbonylmethyl)pyrrolidin-2-one 15 g of the compound obtained in the previous step are dissolved in 100 ml of ethanol and hydrogenated at RT and at atmospheric pressure in the presence of Raney® nickel. When the theoretical volume of hydrogen to be consumed has been reached, the catalyst is filtered off, the filtrate is evaporated to dryness, the residue is taken up with ether and the mixture is washed with water and dried over $MgSO_4$ to give 12 g of the expected compound.

C) 4-(3,4-Dichlorophenyl)-4-(2-hydroxyethyl)pyrrolidin-2-one 12 g of the product obtained in the previous step and 6 g of calcium borohydride are dissolved in 50 ml of THF. After stirring for 2 hours at 0° C., the reaction medium is allowed to return to RT and is then poured into water and acidified to pH 1 by the addition of concentrated hydrochloric acid solution. Extraction is carried out with ethyl acetate and the extract is washed with water and dried over $MgSO_4$. The residue is chromatographed on silica using a DCM/MeOH mixture (100/5; v/v) as the eluent to give 10 g of the expected compound.

D) 4-(3,4-Dichlorophenyl)-4-[2-(tetrahydropyran-2-yloxy)ethyl]pyrrolidin-2-one

A solution of 3 g of 3,4-dihydro-2H-pyran in 10 ml of THF is added dropwise at 0° C. to a solution of 10 g of the product obtained in the previous step in 50 ml of DCM with 0.1 g of paratoluenesulfonic acid. The mixture is then left to stand overnight at RT and evaporated to dryness, the residue is taken up with ether and the mixture is washed with water and with saturated $NaHCO_3$ solution and dried over $MgSO_4$. The residue is chromatographed on silica using a DCM/MeOH mixture (100/5; v/v) as the eluent to give 12 g of the expected compound.

PREPARATION 5

5-(3,4-Dichlorophenyl)-5-[3-(tetrahydropyran-2-yloxy)propyl]piperid-2-one

A) 2-(3,4-Dichlorophenyl)-5-(tetrahydropyran-2-yloxy)pentanenitrile 2.8 g of sodium hydride as a 60% dispersion in oil are added in small portions at RT to a solution of 13.35 g of 3,4-dichlorophenylacetonitrile in 100 ml of THF and the reaction mixture is stirred for 3 hours at RT. It is cooled to −20° C., a solution of 16 g of 2-(3-bromopropoxy) tetrahydropyran in 30 ml of THF is added dropwise and the reaction mixture is stirred for 3 hours while the temperature is allowed to rise to RT. It is concentrated under vacuum, the residue is extracted with ether, the organic phase is washed with water, with a buffer solution of pH 4 and with water and dried over MgSo$_4$ and the solvent is evaporated off under vacuum. The residue is chromatographed on silica using a toluene/AcOEt mixture (100/3; v/v) as the eluent to give 11 g of the expected product.

B) Ethyl 4-cyano-4-(3,4-dichlorophenyl)-7-(tetrahydropyran-2-yloxy)heptanoate 3.3 g of ethyl acrylate are added dropwise at RT to a solution of 11 g of the compound obtained in the previous step and 1 ml of Triton B in 25 ml of dioxane and the reaction mixture is then stirred for 1 hour at RT. It is diluted by the addition of 200 ml of ether, the organic phase is washed four times with water and with saturated sodium chloride solution and dried over MgSO$_4$ and the solvent is evaporated off under vacuum to give 11 g of the expected product.

C) 5-(3,4-Dichlorophenyl)-5-[3-(tetrahydropyran-2-yloxy)propyl]piperid-2-one

A mixture of 11 g of the compound obtained in the previous step, 1 g of Raney® nickel and 0.77 g of NaHCO$_3$ in 120 ml of 95° EtOH is hydrogenated at 40° C. and under 10.2 bar. The catalyst is filtered off on Célite® and the filtrate is concentrated under vacuum. The residue is extracted with DCM, the organic phase is washed with water and with saturated sodium chloride solution and dried over MgSO$_4$ and the solvent is evaporated off under vacuum. The residue is chromatographed graphed on silica using a DCM/MeOH mixture (97/3; v/v) as the eluent to give 6.8 g of the expected product.

EXAMPLE 1

1-[2-[1-[3,5-Bis(trifluoromethyl)benzyl]-5-(3,4-dichlorophenyl)-2-oxopiperid-5-yl]-4-phenylquinuclidinium chloride monohydrate

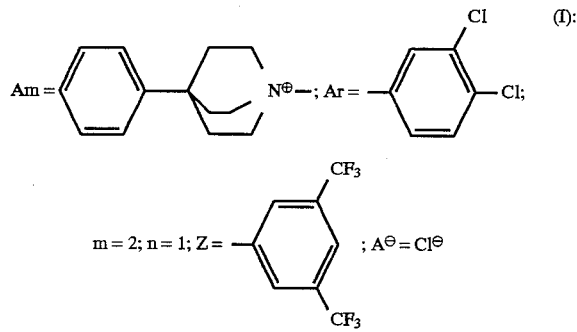

A) 5-(2-Hydroxyethyl)-5-(3,4-dichlorophenyl)-1-[3,5-bis(trifluoromethyl)benzyl]piperid-2-one 1.86 g of the compound obtained in PREPARATION 1 and 0.61 g of potassium tert-butylate in 30 ml of THF are stirred for one hour at RT; 1.54 g of 3,5-bis(trifluoromethyl) benzyl bromide are added and the reaction medium is heated at 50° C. for 2 hours. It is evaporated to dryness. The residue is taken up with 25 ml of methanol and cooled to 0° C., a saturated solution of hydrochloric acid in ether is added until the pH is 1, and the mixture is then evaporated to dryness. The residue obtained is taken up with ethyl acetate, washed 3 times with water and dried over MgSO$_4$ and the solvent is evaporated off under vacuum to give 2.6 g of the expected product.

B) 5-(2-Mesyloxyethyl)-5-(3,4-dichlorophenyl)-1-[3,5-bis(trifluoromethyl)benzyl]piperid-2-one A mixture of the product obtained in the previous step (2.6 g) and 0.66 g of triethylamine in 30 ml of DCM is cooled to 0° C. 0.63 g of methanesulfonyl chloride in 10 ml of DCM is then added. After 15 minutes, the mixture is evaporated to dryness, the residue is then extracted with ether, the extract is washed with water and then with saturated sodium chloride solution and dried over MgSo$_4$ and the solvent is evaporated off under vacuum to give 2.95 g of the expected product.

C) 1-[2-[1-[3,5-Bis(trifluoromethyl)benzyl]-5-(3,4-dichlorophenyl)-2-oxopiperid-5-yl]ethyl]-4-phenylquinuclidinium chloride monohydrate A mixture containing the mesylate obtained in the previous step (2.95 g) and 1.41 g of 4-phenylquinuclidine in 1.2 ml of DMF is heated at 80° C. for 3 hours. After evaporation to dryness, the residue is taken up with DCM and subsequently washed twice with 2N hydrochloric acid solution and then with water. It is dried over MgSO$_4$ and concentrated under vacuum and the residue is then chromatographed on silica using a DCM/MeOH mixture (95/5; v/v) as the eluent to give 0.64 g of the expected product after crystallization from pentane. M.p.=158°–160° C.

EXAMPLE 2

1-[2-[1-[3,5-Bis(trifluoromethyl)benzyl]-5-(3,4-difluorophenyl)-2-oxopiperid-5-yl]ethyl]-4-phenylquinuclidinium chloride dihydrate

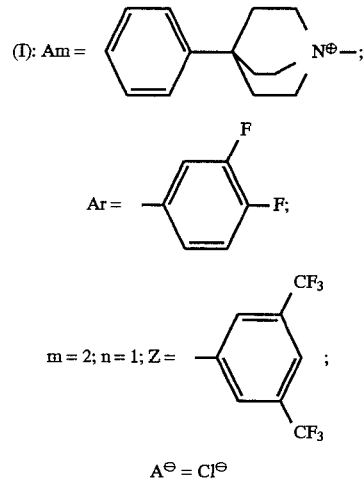

A) 5-(3,4-Difluorophenyl)-5-[2-(tetrahydropyran-2-yloxy)ethyl]-1-[3,5-bis(trifluoromethyl)benzyl]piperid-2-one 5 g of the compound obtained in PREPARATION 2 are dissolved in 90 ml of THF, 1.89 g of potassium tert-butylate are added and the mixture is left to stand for one hour at RT. A solution of 4.75 g of 3,5-bis(trifluoromethyl)benzyl bromide in 30 ml of THF is then added dropwise and the mixture is stirred over-night at RT. It is evaporated, the residue is taken up with water and extracted with AcOEt, the extract is subsequently washed twice with water and then with saturated sodium chloride solution and dried over MgSO$_4$ and the solvent is evaporated off under vacuum to give 8.4 g of the expected product.

B) 5-(3,4-Difluorophenyl)-5-(2-hydroxyethyl)-1-[3,5-bis(trifluoromethyl)benzyl]piperid-2-one The product obtained in the previous step (8.4 g) is dissolved in 70 ml of methanol and a solution of hydrochloric acid in ether is added until the pH is below 1. After 15 minutes, the mixture is evaporated, the residue is taken up with a saturated solution of gaseous HCl in MeOH and the solvent is concentrated under vacuum. The residue is taken up with DCM, washed with 5% NaHCO₃ solution and then with saturated sodium chloride solution and dried over MgSO₄ and the solvent is evaporated off under vacuum to give 5.1 g of the expected product, which crystallizes from ether. M.p.=120° C.

C) 5-(3,4-Difluorophenyl)-5-(2-methanesulfonyloxyethyl)-1-[3,5-bis(trifluoromethyl)benzyl]piperid-2-one A solution of 4 g of the compound obtained in the previous step in 50 ml of DCM is prepared, 1 g of triethylamine is added, the mixture is then cooled in an ice bath and 1.04 g of methanesulfonyl chloride in 20 ml of DCM are added dropwise. The mixture is evaporated, the residue is taken up with water and extracted with AcOEt and the extract is then washed successively with water, 2N HCl solution, water, 5% NaHCO₃ solution, water and saturated sodium chloride solution. It is dried over MgSO₄ and the solvent is evaporated off under vacuum to give 4.7 g of the expected product.

D) 1-[2-[1-[3,5-Bis(trifluoromethyl)benzyl]-5-(3,4-difluorophenyl)-2-oxopiperid-5-yl-]ethyl]-4-phenylquinuclidinium chloride dihydrate 0.60 g of 4-phenylquinuclidine and 1.5 g of the product obtained in the previous step are mixed in the minimum amount of DMF and the mixture is heated at 100° C. for 3 hours. It is allowed to return to RT and evaporated, the residue is taken up with DCM and then washed successively with water, 2N HCl solution (3 times), water and saturated sodium chloride solution and dried over MgSO₄ and the solvent is evaporated off under vacuum to give 1 g of the expected product after trituration in ether, followed by wringing. M.p.=125° C.

EXAMPLE 3

1-[2-[1-[3,5-Bis(trifluoromethyl)benzyl]-6-(3,4-dichlorophenyl)-2-oxoperhydroazepin-6-yl]ethyl]-4-phenylquinuclidinium chloride monohydrate

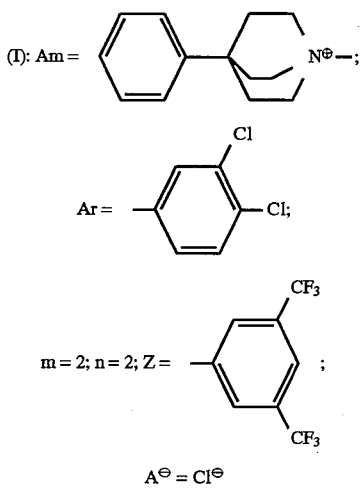

A) 6-(3,4-Dichlorophenyl)-6-[2-(tetrahydropyran-2-yl)ethyl]-1-[3,5-bis(trifluoromethyl)benzyl]perhydroazepin-2-one 1 g of the compound obtained in PREPARATION 3 is dissolved in 15 ml of THF, 0.33 g of potassium tertbutylate is added, the mixture is left to stand for 1 hour at RT and 0.71 g of 3,5-bis(trifluoromethyl)benzyl chloride in 5 ml of THF is then added dropwise. After 2 hours, the mixture is evaporated, the residue is taken up with water and extracted with AcOEt and the extract is then washed with water and with saturated sodium chloride solution. It is dried over MgSO₄ and the solvent is evaporated off under vacuum to give 1.5 g of the expected product.

B) 6-(3,4-Dichlorophenyl)-6-(2-hydroxyethyl)-1-[3,5-bis(trifluoromethyl)benzyl]perhydroazepin-2-one 1.5 g of the product obtained in the previous step are dissolved in 20 ml of methanol and a saturated solution of hydrochloric acid in ether is added until the pH is below 1. After 15 minutes, the mixture is evaporated and the residue is taken up twice with a saturated solution of hydrochloric acid in methanol and evaporated to dryness to give 1.4 g of the expected product.

C) 6-(3,4-Dichlorophenyl)-6-(2-methanesulfonyloxyethyl)-1-[3,5-bis(trifluoromethyl)benzyl]perhydroazepin-2-one 1.4 g of the product obtained in the previous step are dissolved in 15 ml of DCM, 0.32 g of triethylamine is added and the medium is cooled in an ice bath. 0.33 g of methanesulfonyl chloride in 5 ml of DCM is added dropwise and the mixture is allowed to return to RT. It is evaporated, the residue is taken up with water and extracted with AcOEt and the extract is then washed with water and with saturated sodium chloride solution. It is dried over MgSO₄, the solvent is evaporated off and the residue is then chromatographed on silica using DCM and then a DCM/MeOH mixture (99/1; v/v) as the eluent to give 1.3 g of the expected product.

D) 1-[2-[1-[3,5-Bis(trifluoromethyl)benzyl]-6-(3,4-dichlorophenyl)-2-oxoperhydroazepin-6-yl]ethyl]-4-phenylquinuclidinium chloride monohydrate 0.48 g of 4-phenylquinuclidine and 1.3 g of the product obtained in the previous step are mixed in the minimum amount of DMF and the mixture is heated at 100° C. for 5 hours. 0.63 g of sodium iodide is then added and heating is maintained for 1 hour. The mixture is allowed to return to RT, the solvent is evaporated off and the residue is then taken up with water and extracted with DCM. The extract is washed with water and with saturated sodium chloride solution and dried over MgSO₄ and the solvent is evaporated off. The residue is taken up with ethanol and the medium is then passed over an IRA68 resin in hydrochloric acid form. The product is evaporated and the residue is taken up with DCM and washed 3 times with water, twice with 2N HCl solution, a further twice with water and then with saturated sodium chloride solution. It is dried over MgSO₄ and the solvent is evaporated off. The expected product is triturated in ether and then wrung to give 0.8 g. M.p.=157° C.

The compounds described in Table 1 below were also prepared by the procedure of EXAMPLE 1.

TABLE 1

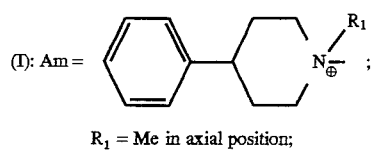

| EXAMPLE no. | Z | Solvate; m.p. °C. |
|---|---|---|
| 4 | 3,5-dimethylphenyl | 2H$_2$O 154–156 |
| 5 | 2,4-bis(trifluoromethyl)phenyl | 2.5H$_2$O 148–150 |
| 6 | 3-trifluoromethylphenyl | 2H$_2$O 164–166 |

EXAMPLES 7 and 8

1-Methyl-1-[2-[1-[3,5-bis(trifluoromethyl)-benzyl]-5-(3,4-dichlorophenyl)-2-oxopiperid-5-yl]-ethyl]-4-phenylpiperidinium iodide (axial isomer and equatorial isomer)

EXAMPLE 7

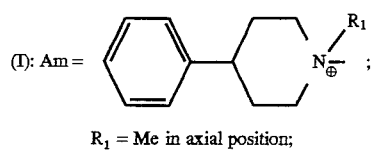

R$_1$ = Me in axial position;

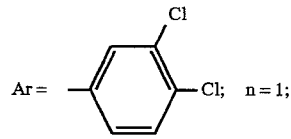

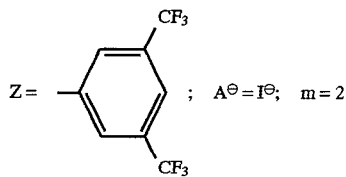

EXAMPLE 8

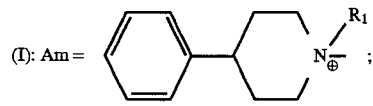

R$_1$ = Me in equatorial position;

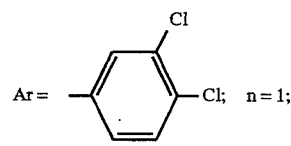

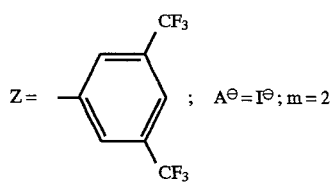

A) 1-[2-[1-[3,5-Bis(trifluoromethyl)benzyl]-5-(3,4-dichlorophenyl)-2-oxopiperid-5-yl]ethyl]-4-phenylpiperidine hydrochloride 2.79 g of 5-(2-mesyloxyethyl)-5-(3,4-dichlorophenyl)-1-[3,5-bis(trifluoromethyl)benzyl]piperid-2-one prepared in Example 1, step B, 1.95 g of K$_2$CO$_3$ and 0.91 g of 4-phenylpiperidine are mixed in 6 ml of acetonitrile and 6 ml of DMF and the mixture is heated at 80° C. for 4 hours. After evaporation of the solvents, the residue is extracted with ethyl acetate and the extract is washed with water and then with saturated NaCl solution. It is dried over MgSO$_4$ and concentrated and the residue is then chromatographed on silica using DCM/MeOH (100/1; v/v) as the eluent. A sample of the product obtained is taken up with a solution of hydrochloric acid in ether and the solvent is evaporated off to give 0.365 g of the expected product, which crystallizes from a pentane/ether mixture. M.p.=170° C.

B) 1-Methyl-1-[2-[1-[3,5-bis(trifluoromethyl)benzyl]-5-(3,4-dichlorophenyl)-2-oxopiperid-5-yl]ethyl]-4-phenylpiperidinium iodide (axial isomer and equatorial isomer)

A mixture comprising 1.1 g of the compound prepared in the previous step, in the form of the base, and 10 ml of methyl iodide is stirred for 18 hours at RT. The excess methyl iodide is evaporated off, the residue is taken up with ether, the product is filtered off and then taken up with DCM and the mixture is evaporated. The residue is chromatographed on silica. Elution with a DCM/MeOH mixture (100/3; v/v) gives the less polar compound, in which the methyl is in the axial position on the piperidine nitrogen. M.p.=128° C. Elution with a DCM/MeOH mixture (100/15; v/v) gives the more polar compound, in which the methyl is in the equatorial position on the piperidine nitrogen. M.p.= 166° C.

EXAMPLE 9

1-[2-[1-[3,5-Bis(trifluoromethyl)benzyl]-4-(3,4-dichlorophenyl)-2-oxopyrrolidin-4-yl]ethyl]-4-phenylquinuclidinium chloride dihydrate

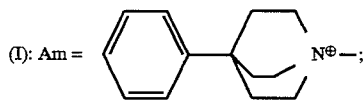

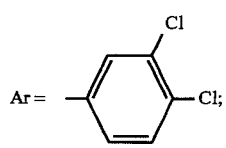

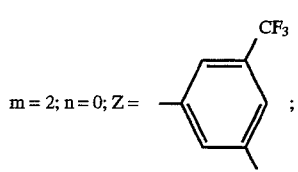

A) 4-(3,4-Dichlorophenyl)-1-[3,5-bis(trifluoromethyl)benzyl]-4-[2-(tetrahydropyran-2-yloxy)-ethyl]pyrrolidin-2-one A mixture containing 3 g of the compound obtained in Preparation 4 and 0.959 g of potassium tertbutylate in 80 ml of THF is stirred for 1 hour at RT, 2.24 g of 3,5-bis(trifluoromethyl)benzyl chloride are then added and the mixture is heated at 50° C. for 3 hours. It is cooled to RT, the solvents are evaporated off, the residue is then extracted with AcOEt and the extract is washed with water and with saturated sodium chloride solution. The organic phase is dried over MgSO$_4$ and then concentrated and the residue is chromatographed on silica using DCM/MeOH (100/1; v/v) as the eluent to give 2.3 g of the expected product.

B) 4-(3,4-Dichlorophenyl)-1-[3,5-bis(trifluoromethyl) benzyl]-4-[2-(mesyloxy)ethyl]pyrrolidin-2-one 2.3 g of the compound obtained in the previous step are dissolved in 100 ml of methanol and a saturated solution of hydrochloric acid in ether is added until the pH is below 1. The mixture is stirred for 15 minutes and evaporated, the residue is taken up with AcOEt and the extract is washed with water and then with saturated sodium chloride solution. It is dried over Na$_2$SO$_4$ and evaporated. 2 g of the resulting alcohol are placed in 50 ml of DCM in the presence of 0.61 g of triethylamine, a solution containing 0.51 g of methanesulfonyl chloride and 10 ml of DCM is added dropwise in the cold and the reaction medium is then stirred at RT for 15 minutes. It is evaporated, the residue is extracted with AcOEt and the extract is washed with water and then with saturated sodium chloride solution. After drying over Na$_2$SO$_4$ and evaporation of the solvent, 2 g of the expected product are obtained.

C) 1-[2-[1-[3,5-Bis(trifluoromethyl)benzyl]-4-(3,4-dichlorophenyl)-2-oxopyrrolidin-4yl]-ethyl]-4-phenylquinuclidinium chloride dihydrate A mixture containing 1.12 g of the compound obtained in the previous step and 0.544 g of 4-phenylquinuclidine in 2 ml of DMF is heated at 80° C. for 4 hours. It is cooled to RT and ice and water are then added. The reaction medium is extracted with DCM and the extract is subsequently washed 6 times with 2N HCl and then with water and with saturated sodium chloride solution. It is dried over Na$_2$SO$_4$ and the solvent is evaporated off under vacuum to give 0.78 g of the expected product. M.p.=120°–122° C.

EXAMPLE 10

4-(3,4-Dichlorophenyl)-4-[2-(4-hydroxy-4-phenylpiperid-1-yl)ethyl]-1-[3,5-bis(trifluoromethyl) benzyl]pyrrolidin-2-one hydrochloride

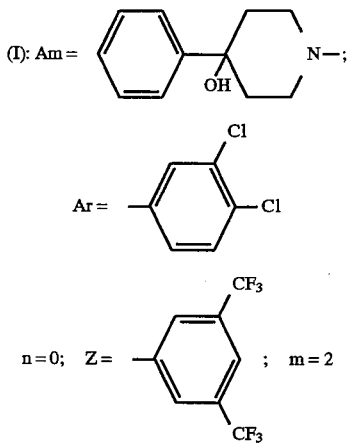

A mixture containing 1 g of 4-(3,4-dichlorophenyl)-1-[3,5-bis(trifluoromethyl)benzyl]-4-]2-(mesyloxy)ethyl] pyrrolidin-2-one obtained in Example 9, step B, 0.875 g of 4-hydroxy-4-phenylpiperidine and 0.483 g of potassium carbonate in 2 ml of DMF is prepared and heated at 80° C. for 3 hours. It is allowed to cool and ice, water and ethyl acetate are then added. Extraction is carried out with AcOEt and the extract is washed with water and then with sodium chloride solution. The pure product is obtained by chromatography on silica using a DCM/MeOH mixture (100/3; v/v) as the eluent. The hydrochloride is then prepared by reaction with hydrochloric acid in DCM. The expected product crystallizes from a pentane/ether mixture. m=0.555 g. M.p.= 136°–138° C.

EXAMPLE 11

4-(3,4-Dichlorophenyl)-4-[2-(4-phenylpiperid-1-yl) ethyl]-1-[3,5-bis(trifluoromethyl)benzyl]pyrrolidin-2-one hydrochloride hemihydrate

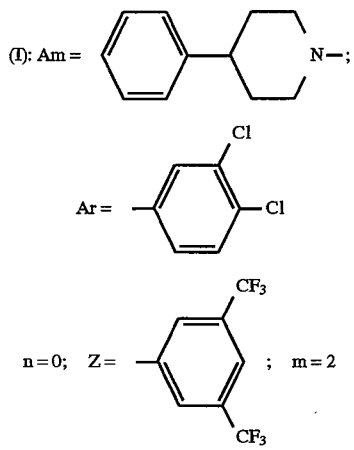

A mixture of 2 g of the compound obtained in step B of EXAMPLE 9, 0.67 g of 4-phenylpiperidine and 1.43 g of potassium carbonate in 6 ml of acetonitrile and 6 ml of DMF is heated at 80° C. for 4 hours. The reaction mixture is concentrated under vacuum, the residue is extracted with AcOEt, the organic phase is washed three times with water and with saturated sodium chloride solution and dried over Na$_2$SO$_4$ and the solvent is evaporated off under vacuum. The residue is chromatographed on silica using a DCM/MeOH mixture (from 100/1; v/v to 100/3; v/v) as the eluent. The product obtained is dissolved in DCM, acidified to pH 1 by the addition of a saturated solution of gaseous HCl in ether and concentrated under vacuum to give 0.39 g of the expected product after crystallization from pentane. M.p.= 126°–130° C.

EXAMPLE 12

1-[3-[1-[3,5-Bis(trifluoromethyl)benzyl]-5-(3,4-dichlorophenyl)-2-oxopiperid-5-yl]propyl]-4-phenylquinuclidinium chloride

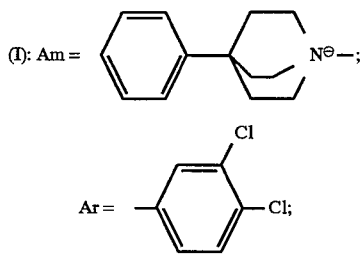

m=3; n=1; Z= 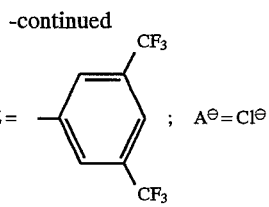 ; A⊖=Cl⊖

A) 5-(3,4-Dichlorophenyl)-5-[3-(tetrahydropyran-2-yloxy)propyl]-1-[3,5-bis(trifluoromethyl)benzyl]piperid-2-one 1.98 g of potassium tert-butylate are added to a solution of 6.8 g of the compound obtained in PREPARATION 5 in 100 ml of THF and the mixture is stirred for 1 hour at RT. 4.62 g of 3,5-bis(trifluoromethyl)benzyl chloride are then added and the reaction mixture is heated at 50° C. for 2 hours. It is concentrated under vacuum, the residue is extracted with AcOEt, the organic phase is washed with water and with saturated NaCl solution and dried over $MgSO_4$ and the solvent is evaporated off under vacuum. The residue is chromatographed on silica using a DCM/MeOH mixture (100/1; v/v) as the eluent to give 10 g of the expected product.

B) 5-(3,4-Dichlorophenyl)-5-(3-hydroxypropyl)-1-[3,5-bis(trifluoromethyl)benzyl]piperid-2-one A saturated solution of gaseous HCl in ether is added to a solution of 10 g of the compound obtained in the previous step in 150 ml of MeOH until the pH is <1, and the mixture is stirred for 10 minutes at RT. It is concentrated under vacuum, the residue is extracted with DCM, the organic phase is washed with water, with 5% $NaHCO_3$ solution and with saturated NaCl solution and dried over $MgSO_4$ and the solvent is evaporated off under vacuum to give 8.8 g of the expected product in the form of an oil.

C) 5-(3,4-Dichlorophenyl)-5-[3-(methanesulfonyloxy)propyl]-1-[3,5-bis(trifluoromethyl)benzyl]piperid-2-one A solution of 8.8 g of the compound obtained in the previous step and 2.51 g of triethylamine in 100 ml of DCM is cooled in an ice bath, a solution of 2.09 g of methanesulfonyl chloride in 20 ml of DCM is added dropwise and the mixture is stirred for 10 minutes. It is concentrated under vacuum, the residue is extracted with AcOEt, the organic phase is washed with water and with saturated NaCl solution and dried over $MgSO_4$ and the solvent is evaporated off under vacuum to give 8.5 g of the expected product.

D) 1-[3-[1-[3,5-Bis(trifluoromethyl)benzyl]-5-(3,4-dichlorophenyl)-2-oxopiperid-5-yl]propyl]-4-phenylquinuclidinium chloride A mixture of 2.41 g of the compound obtained in the previous step and 0.996 g of 4-phenylquinuclidine in 4 ml of DMF is heated at 80° C. for 4 hours. After cooling to RT, the reaction mixture is poured into a water/ice mixture and extracted with DCM, the organic phase is washed with water, four times with 2N HCl solution and three times with saturated NaCl solution and dried over $MgSO_4$ and the solvent is evaporated off under vacuum to give 1.45 g of the expected product after trituration in a pentane/ether mixture, followed by wringing. M.p.=132°–134° C.

What is claimed is:

1. A compound of the formula:

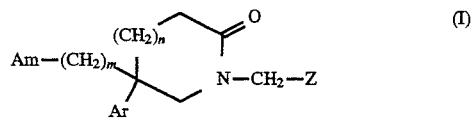

in which:

m is two or three;

n is 0, 1 or 2;

Am is

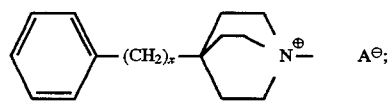

x is zero or one;

Ar is a phenyl which is unsubstituted or monosubstituted or polysubstituted by a halogen atom; a naphthyl; or an indolyl;

Z is a phenyl which is monosubstituted or polysubstituted by a halogen atom, a $(C_1-C_4)$-alkyl or a trifluoromethyl; and $A^\ominus$ is an anion;

the salts thereof, with mineral or organic acids and the solvates thereof.

2. A compound of formula (I) according to claim 1 in which m=2.

3. A compound of formula (I) according to claim 1 in which Z is a group selected from dimethylphenyl, trifluoromethylphenyl and bistrifluoromethylphenyl.

4. A compound according to claim 1 of formula (I) in which:

Ar is a 3,4-dichlorophenyl or a 3,4-difluorophenyl;

Z is a 3,5-dimethylphenyl, a 3,5-bis(trifluoromethyl)phenyl or a 2,4-bis(trifluoromethyl)phenyl;

either n=0, 1 or 2

$A^\ominus$ is a pharmaceutically acceptable anion.

5. A pharmaceutically acceptable salt of a compound of the formula

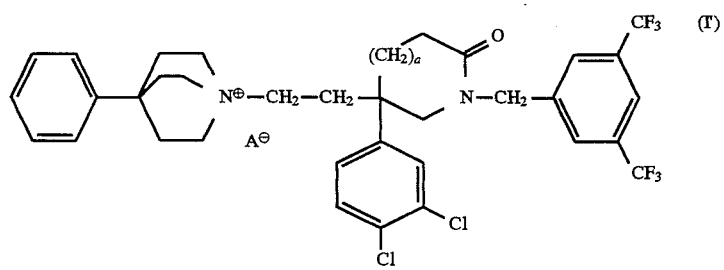

in which a is 0 or 1 and $A^\ominus$ is a pharmaceutically acceptable anion, and the solvates thereof.

6. A method of preparing the compounds of formula (I) according to claim 1, which comprises:

1) treating a compound of the formula

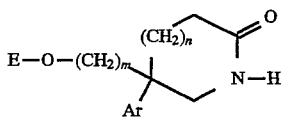

in which m, n and Ar are as defined for (I) in claim 1 and E is an O-protecting group with a halogenated derivative of the formula

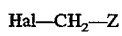

in which Z is as defined for (I) in claim 1 and Hal is a halogen atom;

2) converting the O-protecting group to a hydroxyl group by reaction with an acid or a base;

3) treating the resulting alcohol of the formula

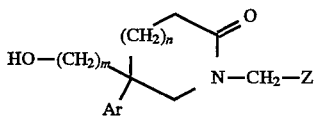

in which m, Ar, Z and n are as defined for (I) in claim 1, with methanesulfonyl chloride, benzenesulfonyl chloride, paratoluenesulfonyl chloride or trifluoromethanesulfonyl chloride;

4) reacting the resulting compound of the formula

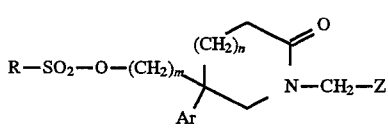

in which R is a methyl, phenyl, paratolyl or trifluoromethyl group, with a secondary or tertiary amine AmH or Am; wherein Am is

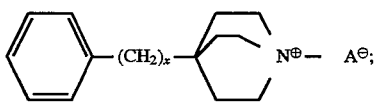

and 5) isolating the resulting product, optionally exchanging the sulfonate anion of the quaternary salt with another anion and optionally converting the resulting product to a salt thereof.

7. A pharmaceutical composition in which a compound according to claim 1, or a pharmaceutically acceptable salt thereof, is present as the active principle.

8. A pharmaceutical composition according to claim 7 in the form of a dosage unit in which the active principle is mixed with at least one pharmaceutical excipient.

9. A pharmaceutical composition according to claim 8 which contains from 0.5 to 1000 mg of active principle.

10. A pharmaceutical composition in which a compound according to claim 2, or a pharmaceutically acceptable salt thereof, is present as the active principle.

11. A pharmaceutical composition in which a compound according to claim 3, or a pharmaceutically acceptable salt thereof, is present as the active principle.

12. A pharmaceutical composition in which a compound according to claim 4, or a pharmaceutically acceptable salt thereof, is present as the active principle.

13. The compound of claim 1 which is 1-[2-[1-[3,5-Bis(trifluoromethyl)benzyl]-5-(3,4-dichlorophenyl)-2-oxopiperid-5-yl]ethyl]-4-phenylquinuclidinium chloride monohydrate.

14. A pharmaceutical composition in which a compound according to claim 13, or a pharmaceutically acceptable salt thereof, is present as the active principle.

15. A pharmaceutical composition in which a compound according to claim 5 or a pharmaceutically acceptable salt thereof, is present as the active principle.

16. A pharmaceutical composition according to claim 15 in the form of a dosage unit in which the active principle is mixed with at least one pharmaceutical excipient.

17. The compound of claim 1 which is 1-[2-[1-[3,5-Bis(trifluoromethyl)benzyl]-5-3,4-dichlorophenyl)-2-oxopiperid-5-yl]ethyl]-4-phenyl-quinuclidinium chloride or a salt or solvate thereof.

18. A pharmaceutical composition in which a compound according to claim 17 or a pharmaceutically acceptable salt or solvate thereof, is present as the active principle.

19. The process of claim 6 wherein the O-protecting group is tetrahydropyran-2-yl, benzoyl or a $C_1$–$C_4$-acyl and Hal is bromine or chlorine.

* * * * *